US010288544B2

(12) United States Patent
Fourno et al.

(10) Patent No.: US 10,288,544 B2
(45) Date of Patent: May 14, 2019

(54) METHOD FOR CHARACTERIZING THE FRACTURE NETWORK OF A FRACTURED RESERVOIR AND METHOD FOR EXPLOITING IT

(71) Applicant: IFP Energies nouvelles, Rueil-Malmaison (FR)

(72) Inventors: Andre Fourno, Rueil-Malmaison (FR); Bernard Bourbiaux, Rueil Malmaison (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 265 days.

(21) Appl. No.: 15/265,665

(22) Filed: Sep. 14, 2016

(65) Prior Publication Data
US 2017/0074770 A1 Mar. 16, 2017

(30) Foreign Application Priority Data
Sep. 15, 2015 (FR) ...................................... 15 58653

(51) Int. Cl.
*E21B 43/26* (2006.01)
*G01N 15/08* (2006.01)
(Continued)

(52) U.S. Cl.
CPC ........... *G01N 15/082* (2013.01); *E21B 41/00* (2013.01); *E21B 41/0092* (2013.01);
(Continued)

(58) Field of Classification Search
CPC .......... E21B 49/00; E21B 43/26; E21B 43/00; E21B 43/267; E21B 43/263; G01V 99/00;
(Continued)

(56) References Cited

U.S. PATENT DOCUMENTS 6,023,656 A 2/2000 Cacas et al.
6,064,944 A 5/2000 Sarda et al.
(Continued)

FOREIGN PATENT DOCUMENTS

FR 2 530 493 A1 1/1984
FR 2 581 767 A1 11/1986
(Continued)

OTHER PUBLICATIONS

B. Bourbiaux et al., "A Rapid and Efficient Methodology to Convert Fractured Reservoir Images into a Dual-Porosity Model", Oil & Gas Science and Technology, vol. 53, No. 6, Nov.-Dec. 1998, pp. 785-799.
(Continued)

*Primary Examiner* — Kandasamy Thangavelu
(74) *Attorney, Agent, or Firm* — Fitch, Even, Tabin & Flannery LLP

(57) ABSTRACT

Method for exploiting a fluid within an underground formation comprising a layer traversed by a fracture network and a well. From property measurements relative to the layer, the fracture network is characterized by statistical parameters and a discrete fracture network model is constructed. For each well, three simplification zones surrounding the well are defined. From the statistical parameters, an equivalent permeability tensor and a parameter characterizing the orientation and the vertical continuity of the fractures are determined for each zone. For each zone, a simplification of the discrete fracture network model is determined as a function of the zone, the equivalent permeability tensor and the value of the parameter. An optimum exploitation scheme is defined for the formation fluid from the simplified fracture network model and a flow simulator.

22 Claims, 4 Drawing Sheets

(51) Int. Cl.
*E21B 43/14* (2006.01)
*E21B 41/00* (2006.01)
*E21B 49/00* (2006.01)
*G01V 99/00* (2009.01)

(52) U.S. Cl.
CPC .............. *E21B 43/14* (2013.01); *E21B 43/26* (2013.01); *E21B 49/00* (2013.01); *G01V 99/00* (2013.01)

(58) Field of Classification Search
CPC . G01V 11/00; G01V 1/50; G01V 1/28; G01V 2210/0646; F23Q 21/00; G06F 17/5009; C09K 8/685; C09K 8/887; G06T 17/20; G06T 17/05
See application file for complete search history.

(56) References Cited

U.S. PATENT DOCUMENTS

| | | | |
|---|---|---|---|
| 6,842,725 | B1 | 1/2005 | Sarda |
| 8,078,405 | B2 | 12/2011 | Delorme et al. |
| 8,688,424 | B2 | 4/2014 | Bourbiaux et al. |
| 8,983,818 | B2 | 3/2015 | Fourno et al. |
| 9,103,194 | B2 | 8/2015 | Khvoenkova et al. |
| 2009/0005996 | A1* | 1/2009 | Delorme ................. E21B 43/00 702/12 |
| 2010/0274547 | A1* | 10/2010 | Bourbiaux ............. G01V 11/00 703/10 |
| 2010/0312529 | A1* | 12/2010 | Souche ................... E21B 43/26 703/2 |
| 2011/0320177 | A1 | 12/2011 | Bowen et al. |
| 2013/0096889 | A1 | 4/2013 | Khvoenkova et al. |
| 2013/0138406 | A1 | 5/2013 | Khvoenkova et al. |
| 2014/0338552 | A1* | 11/2014 | Mace ...................... F23Q 21/00 102/215 |
| 2015/0039234 | A1* | 2/2015 | Abou-Sayed .......... G01V 99/00 702/11 |
| 2015/0355374 | A1* | 12/2015 | Morton ..................... G01V 1/50 703/10 |
| 2016/0123119 | A1* | 5/2016 | Tueckmantel .......... E21B 49/00 703/10 |
| 2016/0266278 | A1* | 9/2016 | Holderby ............... G01V 1/288 |
| 2016/0357883 | A1* | 12/2016 | Weng ..................... E21B 43/26 |

FOREIGN PATENT DOCUMENTS

| | | | |
|---|---|---|---|
| FR | 2 757 947 | A1 | 7/1998 |
| FR | 2 757 957 | A1 | 7/1998 |
| FR | 2 787 219 | A1 | 6/2000 |
| FR | 2 918 179 | A1 | 1/2009 |
| FR | 2 923 930 | A1 | 5/2009 |
| FR | 2 957 200 | A1 | 9/2011 |
| FR | 2 976 099 | A1 | 12/2012 |

OTHER PUBLICATIONS

M. Delorme et al., "Upscaling Improvement for Heterogeneous Fractured Reservoir Using a Geostatistical Connectivity Index", edited in Geostatistics 2008, VIIIth International Geostatistics Congress, Santiago, Chile.

M. Oda, "Permeability Tensor for Discontinuous Rock Masses", Geotechnique, vol. 35, Issue 4, 1985, pp. 483-495.

J.E. Warren et al., "The Behavior of Naturally Fractured Reservoirs", SPE Journal (Sep. 1963), pp. 245-255.

A. Fourno et al., "A Continuum Voxel Approach to Model Flow in 3D Fault Networks: A New Way to Obtain Up-Scaled Hydraulic Conductivity Tensors of Grid Cells", Journal of Hydrology, vol. 493, 2013, pp. 68-80.

* cited by examiner

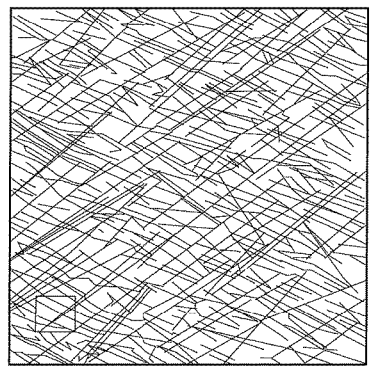
FIG. 1
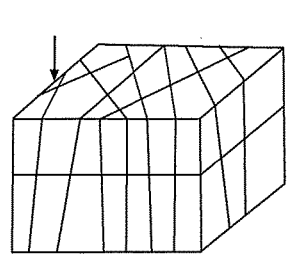 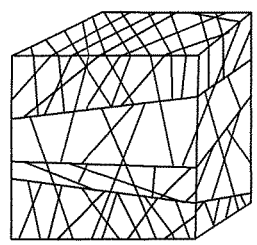 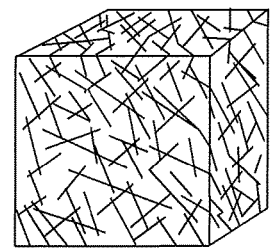
FIG. 2A  FIG. 2B  FIG. 2C

(a, b, c,)~(S1GROS, S2GROS, S3GROS)

METHOD FOR CHARACTERIZING THE FRACTURE NETWORK OF A FRACTURED RESERVOIR AND METHOD FOR EXPLOITING IT

BACKGROUND OF THE INVENTION

Field of the Invention

The present invention relates to the petroleum industry, and more specifically to the exploration and exploitation of hydrocarbon reservoirs or of geological gas storage sites. In particular, the invention relates to a method for constructing a representation of an underground formation traversed by any fracture network and to use of the representation for simulation of fluid flows in the formation.

Description of the Prior Art

Exploration and exploitation of reservoirs, notably petroleum reservoirs, requires knowledge of the underground geology to be as perfect as possible to efficiently provide evaluation of reserves, production modelling or exploitation management. Indeed, determining the location of a production well or of an injection well within a hydrocarbon reservoir, the drilling mud composition, the completion characteristics, selection of a hydrocarbon recovery method (such as waterflooding for example) and of the parameters required for implementing this method (such as injection pressure, production flow rate, etc.) requires good knowledge of the reservoir. Reservoir knowledge notably is as accurate a description as possible of the structure, the petrophysical properties, the fluid properties, etc., of the reservoir being studied.

To acquire such knowledge, the petroleum industry combines field measurements (performed in situ, during seismic surveys, measurements in wells, core drilling, etc.) with experimental modelling (performed in the laboratory) and numerical simulations (using softwares).

Formalization of this knowledge then involves establishing a model of the subsoil, referred to as a "geological model", which accounts for these aspects in an approximate manner. Generally, this type of model is represented on a computer which is then referred to as numerical model. A reservoir model comprises a gridded representation (in form of a regular grid, or more generally in form of a grid pattern), generally three-dimensional, at least one petrophysical property (porosity, permeability, saturation) being assigned to each cell of the gridded representation.

In order to reproduce or to predict (i.e. "simulate") the real hydrocarbon production, reservoir engineers use a computing software referred to as "reservoir simulator". The reservoir simulator is a flow simulator that calculates the flows and the evolution of the pressures within the reservoir represented by a "reservoir mode". If the computing power available for the flow simulations permits, the reservoir model can merge with the geological model. In the opposite case, the reservoir model can be obtained by use of an upscaling technique allowing conversion of the geological model (model with finer cells) to the reservoir model (model with coarser cells). This upscaling stage is well known to reservoir engineers and it can be carried out for example using the CobraFlow software (IFP Energies nouvelles, France).

The results of these computations enables prediction and optimal exploitation schemes (definition of the number of wells to be drilled, their position, the enhanced recovery mode, etc.) for the reservoir being studied in order to improve at least one of the flow rates and the amounts of hydrocarbons recovered. Calculation of the reservoir behaviour according to a given production scenario constitutes a reservoir simulation.

The following documents are mentioned in the description:

Bourbiaux, B., Cacas, M. C., Sarda, S. and Sabathier, J. C., 1998, «A Rapid and Efficient Methodology to Convert Fractured Reservoir Images into a Dual-Porosity Model", Oil & Gas Science and Technology, Vol. 53, No. 6, November-December 1998, 785-799;

Delorme, M., Atfeh, B., Allken, V. and Bourbiaux, B., 2008, Upscaling Improvement for Heterogeneous Fractured Reservoir Using a Geostatistical Connectivity Index, edited in Geostatistics 2008, VIIIth International Geostatistics Congress, Santiago, Chile;

Oda, M., 1985, Permeability tensor for discontinuous Rock Masses, Geotechnique Vol. 35, Issue 4, 483-495;

Warren, J. E. and Root, P. J., "The Behavior of Naturally Fractured Reservoirs", SPE Journal (September 1963), 245-255;

Fourno, A., Grenier, C., Benabderrahmane, A., Delay, F., 2013, A continuum voxel approach to model flow in 3D fault networks: A new way to obtain up-scaled hydraulic conductivity tensors of grid cells, Journal of Hydrology, 493, 68-80.

Fractured reservoirs are an extreme type of heterogeneous geological reservoirs comprising two contrasting media: a matrix medium containing the major part of the oil in place and having low permeability, and a fractured medium representing less than 1% of the oil in place and highly conductive. The fractured medium itself can be complex, having different fracture families characterized by their density, and distributions relative to the length of the fractures of each family, their spatial orientation orientation and their opening. What is referred to as a "fracture" is a plane discontinuity of very small thickness in relation to the extent thereof, representing a rupture plane of a rock of the reservoir.

Those in charge of the exploitation of fractured reservoirs need to as perfectly as possible know the role of the fractures. On the one hand, knowledge of the distribution and of the behavior of these fractures allows optimization of the production schemes of a hydrocarbon reservoir, that is the number of wells to be drilled, their location, their geometry, the type of recovery fluid injected, etc. On the other hand, the geometry of the fracture network conditions the fluid displacement, at reservoir scale as well as local scale where it determines elementary matrix blocks in which the oil is trapped. Knowing the distribution of the fractures is therefore also very helpful to reservoir engineers who want to calibrate the models they construct so that the constructed models reproduce the past production curves, in order to reliably predict future productions. Geosciences specialists therefore have three-dimensional images of reservoirs allowing to locate a large number of fractures.

Considering the complexity of fractured media, often a "double medium" type approach is used to represent this type of medium. This approach, described for example in (Warren J. E. et al., 1963), considers the fractured medium as two continua exchanging fluids with one another: matrix blocks and fractures. This is referred to as "double medium" or "double porosity" model. Thus, "double-medium" modelling of a fractured reservoir discretizes this reservoir into two superposed sets of cells (referred to as grids) making up the "fracture" grid and the "matrix" grid. Each elementary volume of the fractured reservoir is thus conceptually represented by two cells, a "fracture" cell and a "matrix" cell, coupled to one another (i.e. exchanging fluids). In the reality of the fractured field, these two cells represent all of the matrix blocks delimited by fractures present at this point of the reservoir. Indeed, in most cases, the cells have hectometric lateral dimensions (commonly 100 or 200 m) considering the size of the fields and the limited possibilities of simulation softwares in terms of computing capacity and time. The result thereof is that, for most fractured fields, the fractured reservoir elementary volume (cell) comprises innumerable fractures forming a complex network that delimits multiple matrix blocks of variable dimensions and shapes according to the geological context. Each constituent real block exchanges fluids with the surrounding fractures at a rate (flow rate) that is specific thereto since it depends on the dimensions and on the shape of this particular block.

In the face of such a geometrical complexity of the real medium, the reservoir engineers approach is, for each reservoir elementary volume (cell), in representing the real fractured medium as a set of matrix blocks that are all identical, parallelepipedic, delimited by an orthogonal and regular network of fractures oriented in the principal directions of flow. For each cell, the so-called "equivalent" permeabilities of this fracture network are thus determined and a matrix block referred to as "representative" (of the real (geological) distribution of the blocks), single and of parallelepipedic shape, is defined. It is then possible to formulate and to calculate the matrix-fracture exchange flows for this "representative" block and to multiply the result by the number of such blocks in the elementary volume (cell) to obtain the flow at the scale of this cell.

It can however be noted that calculation of the equivalent permeabilities requires knowledge of the flow properties (that is the conductivities) of the discrete fractures of the geological model. It is therefore necessary, prior to constructing this equivalent reservoir model (referred to as "double-medium reservoir model") as described above, to simulate the flow responses of some wells (transient or pseudo-permanent flow tests, also referred to as well tests, interference tests, flow rate tests, etc.) on models extracted from the reservoir model giving a discrete (realistic) representation of the fractures supplying these wells. Adjustment of at least one of the simulated pressure and flow rate responses on the field measurements allows the conductivities of the fracture families to be calibrated. Although it covers a limited area (drainage area) around the well only, such a well test simulation model still comprises a very large number of calculation nodes if the fracture network is dense. Consequently, at least one of the size of the systems to be solved and the computation time often remain prohibitive.

PRIOR ART

Patent application FR-2,967,200 (U.S. Pat. No. 8,983,818) discloses a method allowing simplification of the fracture networks at the local scale of the well drainage area in order to be able to simulate, within a reasonable computation time, the fractured reservoir well tests and thus to calibrate the conductivities of the fracture families. This hydraulic fracture calibration leads to a set of parameters characterizing the fracture network (or fracture model). This fracture model is subsequently used to construct a double medium flow model at the reservoir scale. However, this method is only suited for fracture networks substantially orthogonal to the layers and continuous from one layer to another, that is fracture networks whose flow behaviour is comparable to a 2D behaviour (see notably patent applications FR-2,530,493 corresponding to U.S. Pat. No. 9,103,194 and FR-2,581,767 corresponding to U.S. Ser. No. 13/644,479, as well as document (Fourno et al., 2013). An example of such a fracture network is given in FIG. 2a. In this example, the formation comprises two layers, the fracture network is continuous from one layer to another (thus providing connectivity from one layer to another) and the fractures are substantially orthogonal to the layer boundaries.

Patent applications FR-2,530,493 corresponding to U.S. Pat. No. 9,103,194 and FR-2,581,767 corresponding to US published application 2013/0,096,889 allow accounting for fracture networks that are not at least one of necessarily sub-orthogonal and continuous from one layer to another, while limiting the number of computation nodes. To achieve this, patent application FR-2,530,493 corresponding to U.S. Pat. No. 9,103,194 is based on the use of a Voronoi diagram on each fracture plane, in order to construct a fractured medium grid that gives a good estimation of the volumes in presence at each node and current lines representing the displacement of the fluids node to node. Thus, the grids only comprise 3 or 4 nodes at the intersections, allowing processing of millions of fractures within a reasonable computation time. Patent application FR-2,581,767 corresponding to US published application 2013/0,096,889 allows going beyond the restrictive hypothesis of having as many fracture nodes as matrix nodes while preserving the volumes in place and the flow physics by use of an upwind scheme. Using tree (in particular octree) type structures allows acceleration of the construction of the fracture medium grid (limitation of the number of intersection computations), to simplify the computation of at least one matrix and fracture exchange terms and to properly estimate the matrix volumes associated with the fracture nodes. This method, applied here to the gridding of a dual medium in 3D, applies to any dual problem involving great heterogeneities. Thus, patent applications FR-2,530,493 corresponding to U.S. Pat. No. 9,103,194 and FR-2,581,767 corresponding to US published application 2013/0,096,889 allows representing the fracture networks which are not necessarily at least one of sub-orthogonal and continuous from one layer to another, 3D flow simulations on these 3D fracture networks, carried out using a 3D flow simulator, have allowed having better knowledge of the 3D flows in the reservoirs being studied. However, these methods remain prohibitive today in terms of computation time, notably when a large number of flow simulations (at reservoir scale or at the scale of a zone of influence of one or more wells) is required (case of production scheme optimization, production history matching or calibration of the statistical parameters of fracture families using parameter sensitivity procedures).

SUMMARY OF THE INVENTION

The present invention concerns a method for suitably representing an underground formation comprising a fracture network having at least one family of which can be characterized by any at least one of a dip and a variable continuity of the fractures from one layer to another. In particular, the present invention establishes a parameter allowing qualifying the fracture type and adjusts, according to this parameter, the simplification of the fractured medium. Furthermore, this simplification is not localized to the local scale of the well drainage area, it can be achieved directly at the reservoir scale. This simplified fracture model, is suited to the new generation of 3D reservoir simulators, is subsequently used to optimize the production schemes of the fluid contained in the formation studied, within reasonable computation times.

The present invention thus relates to a method for exploiting a fluid within an underground formation comprising at least one layer traversed by a fracture network and by at least one well, wherein a gridded representation of the at least one layer is constructed from property measurements relative to the at least one layer, and a zone of interest comprising a set of cells of the gridded representation relative to said layer and including at least the well is defined for at least the at least one layer. The method comprises at least the following stages for each one of the layers:

A. from the measurements, characterizing the fracture network with statistical parameters and constructing, from the parameters, a discrete fracture network model;
B. for each one of the wells contained in the zone of interest, defining at least three simplification zones (ZS1, ZS2, ZS3), a first simplification zone (ZS1) containing the well, a second simplification zone (ZS2) having as an inner boundary the outer boundary of the first zone (ZS1) and a third simplification zone (ZS3) having as an inner boundary the outer boundary of the second zone (ZS2) with all of the simplification zones of all of the wells covering all of the cells of the zone of interest;
C. from at least the statistical parameters, determining, for at least each one of the simplification zones (ZS1, ZS2, ZS3) of the zone of interest, an equivalent permeability tensor and a value of a parameter P characterizing the orientation and the continuity towards other layers of the fractures of the network;
D. determining a simplification of the model in each one of said simplification zones, as a function of the zone, of the equivalent permeability tensor and of the value of the parameter P.

Then, from the gridded representation, the simplified fracture network model and a flow simulator, an optimum exploitation scheme is defined for the fluid of the formation and said fluid of said formation is exploited according to the optimum exploitation scheme.

Advantageously, the statistical parameters can be selected from among the following parameters: fracture density, fracture length, fracture spatial orientation, fracture opening and fracture distribution within the layer.

Preferably, the simplification zones can be cylinders of vertical axis and elliptical section, centered around the well.

According to an embodiment of the present invention, the major axis of one of the simplification zones can be oriented in a preferential direction of flow, the preferential direction being determined from a diagonalization of the equivalent permeability tensor.

Advantageously, the distance between two of the zones can be determined according to a geometric progression of constant ratio.

According to an embodiment of the present invention, it is possible to not carry out simplification of the fracture network model in the first simplification zone (ZS1), to carry out a first simplification in the second zone (ZS2) and a second simplification in the third zone (ZS3), the second simplification being greater than the first simplification.

According to an embodiment of the invention, at least one of the second and third simplification zones can be divided into annular simplification sub-zones.

Advantageously, the second simplification zones can be divided into columnar simplification sub-zones.

Preferably, the third simplification zones (ZS3) can be divided into locally homogeneous simplification sub-zones.

According to an embodiment of the invention, the parameter P can be determined for at least each one of the simplification zones (ZS1, ZS2, ZS3), by use of:

a value of a parameter PO measuring the spatial orientation of the fractures of the layer according to a formula:

$$PO = \frac{dev^2}{90^2} - 2\frac{dev}{90} + 1 \text{ with } dev = \arccos(\vec{dir}_3 \cdot \vec{z}) * \frac{180}{(PI)'} \text{ and/or}$$

and/or a value of a parameter PC measuring the continuity of the fractures of the layer towards the other layers according to a formula:

$$PC = \frac{k_3}{(k_1 + k_2)'}$$

where $k_1$, $k_2$ and $k_3$ are the eigenvalues of the permeability tensor after diagonalization.

According to an embodiment of the present invention, the simplification can calculate at least a fracture spacing value for the fractures, an opening value for the fractures and a permeability value.

According to an embodiment of the invention, the simplification of the model can be performed in three spatial directions if parameter P characterizes fractures not substantially orthogonal to at least one of the layers and which are continuous towards the other layers.

According to another embodiment of the invention, the simplification of the model can be performed in two spatial directions if parameter P characterizes fractures substantially orthogonal to the layers and continuous towards the other layers.

Preferably, the optimum exploitation scheme can be defined by determining a recovery method for the fluid, as well as a number, a site and a geometry for injection and production wells allowing to meet predetermined technical and economic criteria.

Advantageously, the exploitation of the fluid according to the optimum exploitation scheme can be at least drilling the injection and production wells and producing the fluid according to the recovery method.

Furthermore, the invention relates to a computer program product which is at least one of downloadable from a communication network, recorded on a computer-readable medium and processor executable, comprising program code instructions for implementing the method according to the above description, when the program is executed on a computer.

BRIEF DESCRIPTION OF THE DRAWINGS

Other features and advantages of the method according to the invention will be clear from reading the description hereafter of embodiments given by way of non-limitative example, with reference to the accompanying figures wherein:

FIG. 1 shows an example of a fracture network along a horizontal section made through a layer of an underground formation;

FIG. 2a illustrates an example of a 2.5D fracture network in the case of an underground formation comprised of two layers;

FIG. 2b shows an example of a 3D fracture network in the case of an underground formation comprised of four layers;

FIG. 2c illustrates an example of a 3D fracture network in the case of an underground formation comprised of a single layer;

DETAILED DESCRIPTION OF THE INVENTION

Figure 3:
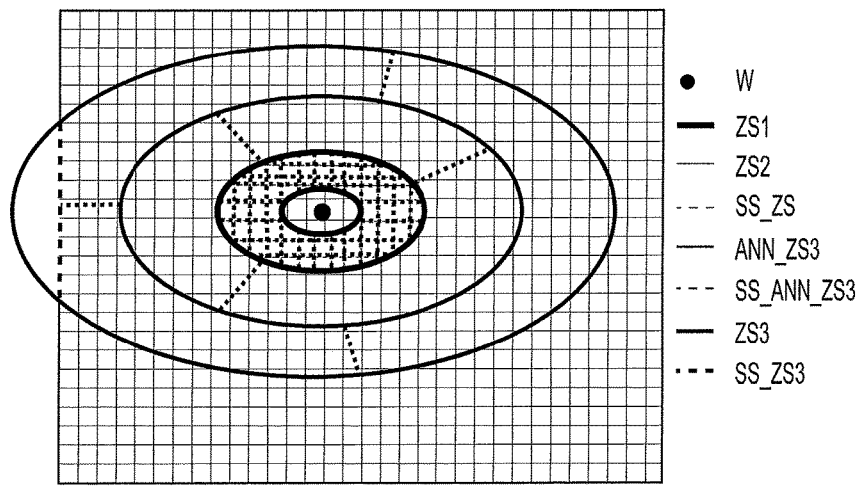
FIG. 3 illustrates the creation of simplification zones and sub-zones around a well traversing a layer of an underground formation.

The following definitions are used in the description of the invention:

Well test is an injection or a production of a fluid in the subsoil at a given well. The well test is characterized by a production curve (amount of fluid injected or produced) and a pressure curve (curve characterizing the pressure evolution in the structure as a function of the production curve). Well tests are useful for calibrating at least one the flow and reservoir models used for flow simulations, Interference test is the combination of several well tests. Each well is characterized by its production curve and its pressure curve. The difference with a single well test per well is that each well can be perturbed by the operation of another one.

The method according to the invention concerns the exploitation of a fluid within an underground formation comprising at least one layer traversed by a fracture network and by at least one well. By way of nonlimitative example, the underground formation has at least one reservoir rock layer (i.e. a rock at least porous and preferably permeable). Fluid exploitation is then referred to as resource exploitation and its goal is to extract the fluid from this reservoir rock. By way of non-limitative example, the fluid in question is of hydrocarbon type (oil, gas, bitumen, etc.).

An underground formation can have several geological layers with each geological layer comprising its own fracture network and each network can comprise several fracture families. In the description hereafter, for simplification reasons, a "3D fracture network" is understood to be a fracture network comprised of at least one fracture family having any dip (orientation) (FIG. 2c) and/or characterized by a variable continuity of the fractures from one layer to another (FIG. 2b); and a "2.5D fracture network" is understood to be a fracture network comprised of fracture families substantially perpendicular to the layers and whose fractures are continuous from one layer to another (FIG. 2a).

The present invention concerns the consideration of any fracture network in a flow simulation, with reasonable computation times even in the case of a 3D fracture network. The present invention therefore models the fracture network of the layer being considered (see stage 1 described below), then in simplifying it (see stage 2 described below) in order to allow numerical flow simulations (see stage 3 described below) within reasonable computation times.

The present invention requires:

property measurements relative at least to the layer being studied: these can be petrophysical property measurements performed in situ, at different points of the formation being studied, such as porosity, permeability and lithology (i.e. the rock type), relative permeability or capillary pressure. These measurements may have been obtained for example through core drilling, via logging operations carried out in wells or seismic acquisition surveys. They can however also be measurements (oil flow rate, water flow rate, pressure variation for example) related to the flows in the layer being studied, obtained for example by producing the fluid in some wells traversing the formation, during well tests or interference tests, a gridded representation representative of at least the layer being studied which is also referred to as "reservoir model" which is a sort of a subsoil model constructed in order to describe as precisely as possible the structure, the petrophysical properties, the fluid properties of the formation being studied, and at least of the layer being studied. This model is generally represented on a computer and it has a grid with each cell of this grid comprising one or more property values relative to the formation being studied (porosity, permeability, saturation, etc.). A reservoir model must verify as far as possible the properties relative to the layer being studied collected in the field such as logging data measured along wells, measurements performed on rock samples taken in wells, data deduced from seismic acquisition surveys, production data such as oil flow rate, water flow rate, pressure variation, etc. Known reservoir simulations are methods for constructing such a gridded representation of a formation. It is noted that the reservoir model can merge with the geological model when the computing power is sufficient to allow numerical flow simulation calculations on a fine-cell grid. In the opposite case, an upscaling technique can be used to convert a fine-cell grid (geological model) to a model with coarser cells (reservoir model). This upscaling stage can be carried out for example with the CobraFlow software (IFP Energies nouvelles, France), a zone of interest (ZOI) includes a set of cells of the gridded representation relative to the layer studied and comprising at least the well traversing the layer concerned. The dimensions and the geometry of this zone can be variable depending on the embodiment of the present invention being considered. In the most general case, that is during production simulations for the fluid of the formation being studied designed to test different exploitation schemes, the ZOI can correspond to the entire reservoir and it can comprise at least two wells and preferably all of the wells. In cases where, prior to this simulation, a calibration of the model used for the simulation is carried out using well tests, the ZOI being considered advantageously corresponds to a part of the reservoir of kilometric dimension including a single well. In the case of interference tests, the ZOI can then correspond to a portion of the reservoir and comprise several wells. It can be noted that the ZOI can be discontinuous and consist for example of a sum of sub-zones of interest locally defined around a given number of wells, a flow simulator is a numerical program executed on a computer, which is used to predict fluid flows within the various layers of a formation. Flow simulation, also referred to as reservoir simulation, numerically predicts the production of a fluid trapped in one or more layers of an underground formation, production requiring the existence of at least one injection well (into which another fluid intended to expel the trapped fluid is injected) and one production well (to which the expelled trapped fluid is displaced and from where it can be extracted). Advantageously, a "double medium" flow simulator allowing exchanges between the non-fractured rock blocks and the fracture network to be modelled without requiring discretization of these blocks is used. An example of such a simulator is the PUMAFLOW software (IFP Energies nouvelles, France).

The method according to the invention comprises at least the following stages, stages 1 and 2 being repeated for each layer of the formation studied:
1. Fracture Network Modelling
1.1. Determination of statistical parameters
1.2. Construction of a discrete fracture network model
2. Simplification of the Fracture Network Model
2.1. Definition of simplification zones
2.2 Determination of an equivalent permeability tensor
2.3. Determination of a parameter P characterizing the fracture geometry
2.4. Simplification of the discrete fracture network model
3. Formation Fluid Exploitation.

The main stages of the present invention are detailed hereafter. Stages 1 and 2 are described for a single layer of the formation being studied and have to be repeated for all the layers of the formation. Implementation of the invention requires the existence of at least one well traversing each one of the layers being considered, but it does not require taking accounting for all the wells traversing a given layer.

1. Fracture Network Modelling

This stage determines a model of the fracture network of the layer being studied, respecting the property measurements relative to the layer carried out in situ.

This stage can comprise at least the following sub-stages:
1.1. Determination of Statistical Parameters This sub-stage determines statistical parameters allowing characterizing the fracture network of the layer being studied. It requires measurements allowing direct or indirect fracture characterization.

Information on the fracturation of a geological layer can be obtained by from:
- core samples extracted from the formation being studied, from which a statistical study of the intersected fractures can be conducted,
- outcrops, which afford the advantage of providing a large-scale view of the fracture network; and
- seismic images allowing identification of major geological events.

According to the invention, statistical parameters (referred to as PSF hereafter) are used in order to characterize the fractures observed upon measuring. According to an embodiment of the invention, the density of the fractures observed, their length, their spatial orientation, their opening and their distribution within the layer studied are characterized.

Statistical parameters (PSF) describing the fracture network of the layer being studied are thus obtained, from which a model of this network can be constructed, at the scale of each cell of the gridded representation.

1.2. Construction of a Discrete Fracture Network Model

According to the invention, a realistic image of the fracture network characterized by statistical parameters (PSF) determined in the previous sub-stage is then constructed through the agency of a discrete fracture network (DFN) model.

A detailed representation (DFN) of the inner complexity of the fracture network, as true as possible to the direct and indirect reservoir observations, is therefore associated in each cell, from a gridded representation of the formation being studied (and at least of the layer being considered). FIG. 1 shows a horizontal section taken in a layer of a formation and the fracture network, observable at formation scale, for this section. FIG. 2 shows the discrete fracture network visible at the scale of the three-dimensional cell whose 2D limits are represented by the square in FIG. 1. A set of porous matrix blocks of uneven shape and size, delimited by fractures, can be observed in FIG. 2. This discrete fracture network is a representative image of the real network of fractures delimiting the matrix blocks.

Known modelling softwares, such as the FRACAFlow® (IFP Energies nouvelles, France) software, can be used to construct a discrete fracture network (DFN) in each cell of the gridded representation. These softwares use the previously determined statistical parameters (PSF).

2. Simplification of the Fracture Network Model

Owing to its extreme geometrical complexity, the fracture network model (DFN) obtained in the previous stage, representative of the real fractured reservoir, cannot be used to simulate that is at least one of reproduce and predict, the local flows around wells. Indeed, the DFN obtained in the previous stage often comprises a large number of fractures and many intersection points between fractures. The grid will therefore be too complex or have too many computation nodes, thus making simulations prohibitive in terms of computation time. The goal of this stage is to determine a simplified fracture network model however respecting the in-situ flow measurements.

Thus, this stage simplifies the discrete fracture network model determined in the previous stage for the layer being considered. According to the invention, this simplification is different depending on the simplification zones described around each well considered for the layer in question (see stage 2.1). Each simplification zone is characterized by 2 parameters specific thereto: an equivalent permeability tensor (see stage 2.2) and a parameter (P) characterizing both the orientation and the continuity (towards the other layers of the formation studied) of the fracture network of this layer (see stage 2.3).

2.1. Definition of Simplification Zones

This sub-stage defines simplification zones for each well being considered. According to the invention, at least three simplification zones (ZS1, ZS2, ZS3) are defined around each well, the first of the simplification zones (ZS1) contains the well, the second of said simplification zones (ZS2) having as its inner boundary the outer boundary of the first zone (ZS1) and the third of the simplification zones (ZS3) has as its inner boundary the outer boundary of the second zone (ZS2).

Furthermore, according to the invention, all of the simplification zones for all the wells being considered must cover all of the cells of the ZOI, whatever the number of wells. The invention is not limited to the definition of three simplification zones for each well being considered, and an implementation of the invention can be achieved for NZ simplification zones, with NZ≥3.

According to a preferred embodiment of the invention, the simplification zones correspond to cylinders of elliptical section, and the axis of revolution of the cylinders can be oriented along a vertical axis (see for example the horizontal sections of zones ZS1, ZS2 and ZS3 created around a well W in FIG. 3). The sections in a horizontal plane of the simplification zones are then ellipses (ZS1) or elliptical crowns (ZS2 and ZS3), concentric and centered around a well. According to another embodiment of the invention, the simplification zones correspond to cylinders of elliptical section, and the axis of revolution of the cylinders can be oriented along an axis defined by the perpendicular to the dip (slope line) of the layer considered, or an axis defined by the axis of the well considered.

According to an embodiment of the invention, at least one of a simplification zone ZS2 and a simplification zone ZS3 is divided into N simplification sub-zones by adding, between the inner and outer boundaries of the zone being considered, N−1 intermediate boundaries, and the geometry of the intermediate boundary n (with n ranging between 1 and N−1) can result from a linear combination (for example function of n and N) of the curves describing the inner and outer boundaries of the simplification zone being considered. For example, in the case of a cylindrical simplification zone of elliptical section, dividing this simplification zone into two simplification sub-zones amounts to adding an intermediate cylindrical boundary (see for example boundary ann_ZS3 in FIG. 3) of elliptical section. This type of simplification sub-zone is referred to as "annular sub-zone" hereafter. This embodiment is preferably selected in case of relatively homogeneous flow properties.

According to an embodiment where the simplification zones or the simplification sub-zones are cylinders of horizontal section with elliptical geometry, the ellipses can be more preferably oriented (direction of the major axis of each ellipse) as a function of the preferential flow directions deduced from an equivalent permeability computation. Such a computation is precisely described in the next sub-stage. Likewise, the aspect ratio of the ellipse (by denoting by $L_{max}$ the half-length of the major axis of the ellipse, and by $L_{min}$ the half-length of the minor axis of the ellipse, this aspect ratio is defined by $L_{max}/L_{min}$) and the distance between concentric ellipses (distance between the inner and outer elliptical boundaries of a given concentric crown) can be determined as a function of the flow anisotropy in the layer studied.

According to a particular embodiment of the invention, the aspect ratio can be defined according to a formula of the type:

$$\frac{L_{max}}{L_{min}} = \sqrt{\frac{\max(k_1, k_2)}{\min(k_1, k_2)}}$$

where $k_1$ and $k_2$ are respectively the eigenvalues, obtained after diagonalization of the equivalent permeability tensor, in the principal directions closest to a horizontal plane.

According to another particular embodiment of the invention, the distance between concentric ellipses (boundaries between zones) can be defined by means use of a dimensioning criterion in accordance with a modelling accuracy uniformly distributed over the simulation domain, which sets the half-lengths of the major axis $L_{max}$ (or of the minor axis $L_{min}$) of 2 successive ellipses I and i+1 (with i ranging from 1 to I, and I at least equal to 3) at values in geometric progression of constant ratio r (equal to 2 for example), according to a formula of the type:

$$\frac{L_{max(i+1)}}{L_{max(i)}} = \frac{L_{min(i+1)}}{L_{min(i)}} = r.$$

This rule allows giving an equal weight to each zone i (i=1 to I, I≥3) in terms of pressure difference observed in each crown under permanent flow regime conditions.

According to a preferred embodiment of the invention, a simplification zone ZS2 is divided into a number of sub-zones equal to the number of cell columns present in zone ZS2. The term "cell column" is used to designate a "pile" of vertical cells of the gridded representation. These sub-zones are then quadrilaterals whose side lengths correspond to the discretization along axes x and y of the gridded representation (sub-zones ss_ZS2 in FIG. 3). This type of simplification sub-zone is referred to as "columnar simplification sub-zone" hereafter.

According to a preferred embodiment of the invention, a simplification zone ZS3 is divided into simplification sub-zones by accounting for the flow property heterogeneities. By way of non-limitative example, it is possible to delimit simplification sub-zones of a zone ZS3 by grouping together sub-sets of cells having similar flow properties. For example, in the case of a zone ZS3 corresponding to a cylinder of vertical axis with elliptical section, an angular scan centered on the well is performed. The cells contained per sampled degree are grouped together into a cell column. Thus, zone ZS3 is characterized by at most 360 cell columns. For each one of these cell columns, the equivalent fracture permeability tensor is calculated (see next stage). This tensor allows characterizing the dynamic properties of the fracture network of the cell column being studied. The permeability values and the flow orientation obtained are then compared among neighboring cell columns. If the equivalent properties of two neighboring cell columns are similar, these two cell columns are considered to belong to the same sub-zone. In the opposite case (20% difference on the principal permeability values or 10 degree difference on the principal permeability directions for example), the two cell columns are assigned to different sub-zones. Thus, the outer limit, in a horizontal plane, of the zone ZS3 being considered is divided into arcs of elliptical shape (see FIG. 3). The limits in a horizontal plane of the sub-zones are then obtained by connecting the end points of each arc to the centre (well W) of the ellipse (dotted lines ss_ann_ZS3 and ss_ZS3 in FIG. 3): each sub-zone to be simplified is thus defined as the union of sub-sets of cells forming the area contained between the intra-zone radial partition (dotted lines ss_ann_ZS3 and ss_ZS3) and the inter-zone elliptical limits (full lines ann_ZS3 and ZS3). Simplification sub-zones with substantially homogeneous flow properties are thus obtained for zone ZS3, each one being characterized by a specific equivalent permeability. This type of simplification sub-zone is referred to as "locally homogeneous simplification sub-zone" hereafter.

According to an embodiment of the invention, a division into locally homogeneous simplification sub-zones can be additionally applied to annular type sub-zones for a simplification zone ZS3 (sub-zones ss_ann_ZS3 and ss_ZS3 in FIG. 3).

According to an embodiment of the invention, a division into columnar simplification sub-zones can be additionally applied to annular type sub-zones for a simplification zone ZS2.

2.2 Determination of an Equivalent Permeability Tensor

This sub-stage calculates an equivalent permeability tensor for at least each of the simplification zones being determined in the previous sub-stage, the goal being, in the next sub-stage, to replace the fracture network of each simplification zone by a simplified network having the same flow properties as the initial network.

More preferably, in cases where simplification sub-zones have been defined for a given simplification zone in the previous sub-stage, an equivalent permeability tensor is calculated in each one of these simplification sub-zones.

The equivalent permeability calculation is carried out from the fracture network model DFN, or directly from the PSF. This type of equivalent permeability calculation is well known. The numerical method for calculating equivalent properties of fractured media implemented in the FracaFlow software (IFP Energies nouvelles, France), reminded hereafter, can be used for example.

According to an embodiment of the invention, a permeability tensor representative of the flow properties of the discretized fracture network (DFN) can be obtained, for example, using one of the following two upscaling methods:

a first method, referred to as local analytic upscaling, is based on an analytical approach described for example in document (Oda, 1985) or in patent application FR-2,918,179 corresponding to U.S. Pat. No. 8,078,405. This method affords the advantage of being very fast. Its field of application is however limited to well-connected fracture networks. In the opposite case, significant errors can be observed regarding the permeability tensor;

a second method, numerical, referred to as local numerical upscaling, is described in document (Bourbiaux, et al., 1998) or in patent application FR-2,757,947 corresponding to U.S. Pat. No. 6,023,656 for calculating the equivalent permeabilities. This method is based on the numerical solution of the flow equations on a discrete grid of the fracture network for different boundary conditions applied to the calculation cell column considered. The equivalent permeability tensor is obtained by identification of the ratios between flow rate and pressure drop at the boundaries of the computational domain. This approach, costlier than the previous one, affords the advantage of a well characterizing a given network (even weakly connected).

According to an embodiment of the present invention, in order to make the most of the advantages afforded by the two upscaling methods, the permeability tensor is determined by one or the other of these two methods, for example according to the selection procedure described in document FR-2,918,179 corresponding to U.S. Pat. No. 8,078,405 based on the value of the connectivity index of the fracture network. This index, representative of the ratio between the number of intersections between fractures and the number of fractures, is calculated for each unit of the cell column being considered. It's value allows consideration of the network as very well connected, weakly/badly connected or non-connected. The upscaling method is then selected as described in (Delorme, et al., 2008) and summarized hereafter:

well-connected network: in this case, characterized by a connectivity index close to or exceeding 3 (at least 3 intersections per fracture of the network on average), the analytical upscaling method is selected because its accuracy is guaranteed considering the good connectivity of the network, with the essential additional advantage of fastness, weakly/badly-connected network: in this case, the connectivity index ranges between 1 and 3 (which corresponds to a number of fracture intersections ranging between one and three times the number of fractures), and the numerical upscaling method is selected to reliably calculate the permeability tensor, when the network is very poorly or even not connected (number of intersections close to or lower than the number of fractures), the original fractures (which are few) are kept, and there is no need to simplify the fracture network.

According to an embodiment of the invention, the equivalent permeability tensor thus calculated is diagonalized in order to determine the three principal directions of flow, denoted by $dir_1$, $dir_2$ and $dir_3$ hereafter, direction $dir_1$ ($dir_2$ and $dir_3$ respectively) being so selected that its angle with the X-axis (respectively with the Y-axis, the vertical axis) is the smallest. The eigenvalues of this tensor, associated with the three principal directions $dir_1$, $dir_2$ and $dir_3$, are denoted by $k_1$, $k_2$ and $k_3$ respectively.

According to an embodiment of the invention, a fracture porosity representative of the fracture volume of the zone or the sub-zone is additionally calculated. This porosity $\phi f$ is obtained with a formula of the type:

$$\phi f = \frac{\text{Fracture volume}}{\text{Total volume}}$$

where the volume of the fractures present in the volume being considered can be obtained from the PSF of the DFN determined in stage 1, and Total volume is the total volume of the simplification zone or sub-zone.

According to an embodiment of the invention, the characteristic dimensions of a representative matrix block (referred to as equivalent) are furthermore calculated for each simplification zone, and preferably for each simplification sub-zone. The characteristic dimensions of this matrix block in directions $dir_1$, $dir_2$ and $dir_3$ are denoted by a, b and c respectively. Such a calculation can be carried out with the technique described in patent applications FR-2,757,957 corresponding to U.S. Pat. No. 6,064,944 or FR-2,923,930 corresponding to U.S. Pat. No. 8,688,424.

2.3. Determination of a Parameter P Characterizing the Fracture Geometry

A value of a parameter P characterizing both the spatial orientation and the continuity, towards the other layers of the fracture network, of fractures contained in at least each simplification zone determined in sub-stage 2.1 is determined from at least statistical parameters (PSF) determined in the previous stage. Thus, the value of this parameter P allows determination if the fracture network of interest is of 2.5D or 3D type in each simplification zone.

According to a preferred embodiment of the invention, a parameter P is determined, as the case may be, for each simplification sub-zone defined in stage 2.1, in particular in the case of heterogeneity of the flow properties, and more preferably in cases where so-called locally homogeneous simplification sub-zones have been predetermined.

According to an embodiment of the present invention, a binary parameter P of value 0 or 1 is defined for each simplification (sub-)zone. Value 1 of parameter P indicates that the fracture families of the fracture network contained in a given simplification sub-zone are both substantially orthogonal to the boundaries of the layer considered and substantially continuous towards the other layers of the formation (FIG. 2a). Value 0 indicates that the fracture network of the simplification (sub-)zone being considered comprises at least one fracture family having at least one any dip (FIG. 2c) and characterized by a variable continuity of the fractures from one layer to another (FIG. 2b). In other words, value 1 of parameter P indicates that the fracture network of the simplification (sub-)zone being considered is 2.5D, whereas value 0 of parameter P indicates that the fracture network of the simplification (sub-)zone being considered is 3D.

According to an embodiment of the invention, a parameter PC qualifying the fracturation continuity of a given layer towards the other layers of the formation is determined. This parameter can be calculated per simplification zone or per simplification sub-zone. An equivalent permeability tensor calculated over the height of the layer considered for the simplification (sub-)zone considered is taken into account and this tensor is diagonalized. If $k_3$ (sub-vertical permeability) is very different from $k_1+k_2$ (sum of the sub-horizontal permeabilities), then the fracturation is not continuous over the height of the layer considered for the (sub-)zone considered. More precisely, a parameter PC can be determined with a formula of the type:

$$PC = \frac{k_3}{(k_1+k_2)}.$$

When $PC < \varepsilon_c$, where $\varepsilon_c$ is a predetermined threshold, the fracture network may be considered not to be continuous from one layer to another in the simplification (sub-(zone considered. $\varepsilon_c = 0.8$ is preferably selected. This very restrictive criterion implies that most networks of natural fractures will be dealt with as 3D fracture networks.

According to an embodiment of the invention, a parameter PO qualifying the spatial orientation of the fracturation of a given layer is determined. This parameter can be calculated per simplification zone or per simplification sub-zone. More precisely, an equivalent permeability tensor calculated over the height of the layer considered per simplification (sub-)zone (see sub-stage 2.2) is considered and this tensor is diagonalized. If the principal direction associated with component $k_3$ of this tensor is characterized by a deviation with respect to the normal to the layer lower than a certain predetermined threshold, the fractures are considered to not to be substantially orthogonal for the simplification (sub-)zone being considered. A parameter PO of the form as follows can for example be determined:

$$PO = \frac{dev^2}{90^2} - 2\frac{dev}{90} + 1 \text{ with } dev = \arccos(d\vec{w}_3 \cdot \vec{z}) * \frac{180}{(PI)}$$

arccos giving an angle in radians between [0, PI] converted to degrees so as to obtain dev.

When $PO < \varepsilon_o$, where $\varepsilon_o$ is a predetermined threshold, the fracture network of the layer being considered, for the (sub-)zone considered, is considered not to be substantially orthogonal to the boundaries of the layer considered. $\varepsilon_o = 0.81$ is preferably selected (which corresponds to a 9° deviation with respect to the normal to the layer).

According to an embodiment, the value of parameter P is defined as follows:
parameter P is 1 if both parameter PC and parameter PO are greater than or equal to 0.8. In this case, the fracture network of the layer being considered, for the (sub-)zone considered, is considered to be (substantially) 2.5D;
parameter P is 0 if at least one of parameters PC or PO is strictly less than 0.8. In this case, the fracture network of the layer considered, for the (sub-)zone considered, is considered to be (substantially) 3D.

2.4. Simplification of the Fracture Network

This stage simplifies the fracture network in each cell of the simplification zones defined above (which amounts to simplifying in each cell of zone of interest ZOI, since all the cells of all of the simplification zones correspond to all of the cells of zone of interest ZOI). The simplification is a function of the simplification zone considered, of the equivalent permeability tensor determined above and of the value of parameter (P) characterizing the orientation and the continuity, towards the other layers, of the fractures of the fracture network of the layer being considered.

Thus, according to the invention, simplification of the fracture network model is achieved differently from one simplification zone to another.

According to a preferred embodiment of the invention, simplification is performed as follows:
no simplification of the fracture network model is performed in first simplification zone ZS1. Indeed, simplification zone ZS1 being the closest to the well, it is highly desirable not to simplify the fracture network model to correctly model the transient flow phenomena occurring around the well;
a moderate first simplification is applied in second zone ZS2. Indeed, simplification zone ZS2 is located further from the well being considered than zone ZS1, simplifying the fracture network model may be considered but it is preferred that the local variations of the flow properties in this zone be respected. According to a more preferred embodiment of the invention, a zone ZS2 is simplified by simplification sub-zones. Preferably, the simplification sub-zones of a zone ZS2 are of columnar type (see sub-stage 2.2);
a significant second simplification is performed in third zone ZS3. Since it is further from the well being considered, it is acceptable to be less precise in the detection of heterogeneities than in the case of ZS2 type zones. According to a preferred embodiment of the invention, a zone ZS3 is simplified by simplification sub-zones. Preferably, the simplification sub-zones of a zone ZS3 are of locally homogeneous type (see sub-stage 2.2). Advantageously, a simplification zone ZS3 can first be divided into annular simplification sub-zones prior to dividing the annular type sub-zones into locally homogeneous type sub-zones.

From the division into simplification zones (preferably into simplification sub-zones in the case of a heterogeneous fracture network), from an equivalent permeability value and from a value of a parameter P assigned to each simplification zone (preferably to each simplification sub-zone), a simplified fracture network model (DFNs) is created, equivalent to the initial fracture network model (DFN) in terms of flow per simplification (sub-)zone. The following calculations will be equally applied to a simplification zone or to a simplification sub-zone. The equivalent permeability of a matrix block m of dimension (a,b,c) and the real permeability of the rock (also referred to as matrix) in a cell ijk are denoted by $keq_m^{ijk}$ and $k_m^{ijk}$ respectively hereafter.

According to the invention, at least a fracture spacing value, a fracture opening value and a permeability value, or any combination of these parameters, are determined in this stage.

According to an embodiment of the invention, a fracture spacing $s_1^{gros}$ of the simplified fracture network model (DFNs) in the principal direction of flow $dir_1$ is determined with a formula:

$$s_1^{gros} = DC/NG \qquad (1)$$

where NG is an integer controlling the connectivity. It represents the minimum number of simplified fractures that must intersect the smallest side of the (sub-)zone to be simplified in order to provide connectivity between simplified (sub-)zones; NG=6 is preferably selected; and DC is a characteristic dimension of the (sub-)zone being considered. According to an embodiment of the invention, the characteristic dimension of a (sub-) zone is the smallest length of a quadrilateral inscribed in the (sub-) zone.

According to an embodiment of the invention, if $s_1^{gros}$ is greater than a predetermined threshold $s_1^{max}$, $s_1^{gros}$ is then set to $s_1^{max}$. Advantageously, $s_1^{max} = DC/6$ is used.

According to an embodiment of the invention, the fracture spacing of the simplified fracture network model (DFNs) in the other principal directions of flow $dir_2$ and $dir_3$ is then determined by putting:

$$S_2^{gros} = s_1^{gros} \qquad (2)$$

$$S_3^{gros} = s_1^{gros} \qquad (3).$$

According to an embodiment of the invention for which a characteristic matrix block dimension (a,b,c) has been calculated (see stage 2.2), a (fracture spacing) magnification parameter G is determined with a formula:

$$G = s_1^{gros}/a \qquad (4).$$

According to another embodiment of the invention for which a characteristic matrix block dimension (a,b,c) has not been calculated, G is set equal to 1.

According to an embodiment of the invention, the fracture spacing of the simplified fracture network model (DFNs) in the other principal directions of flow $dir_2$ and $dir_3$ is determined with formulas:

$$S_2^{gros} = G \cdot b \qquad (5)$$

$$S_3^{gros} = G \cdot c \qquad (6).$$

According to a particular embodiment of the invention, fracture conductivities $C_{f1}^{gros}$, $C_{f2}^{gros}$ and $C_{f3}^{gros}$ whose values allow conserving the fluxes, that is also the equivalent permeabilities, can be determined:

$$C_{f1}^{gros} = s_1^{gros} \cdot (-k_1 + k_2 + k_3)/2 \qquad (7)$$

$$C_{f2}^{gros} = s_2^{gros} \cdot (k_1 - k_2 + k_3)/2 \qquad (8)$$

$$C_{f3}^{gros} = s_3^{gros} \cdot (k_1 + k_2 - k_3)/2 \qquad (9)$$

The numbers in indices f1, f2, f3 of the conductivity values indicate the direction of the normal of the simplified fracture. For example, $C_{f1}^{gros}$ is the conductivity to be assigned to the fractures of the coarse network whose normal is oriented in direction $dir_1$, the main direction of flow close to the X-axis of the gridded representation of the layer considered.

According to an embodiment of the invention, a fracture opening $e^{gros}$ allowing conserving the fracture porosity $\phi_f$ of the initial network is calculated with a formula:

$$e^{gros} = \phi_f/(1/s_1^{gros} + 1/s_2^{gros} + 1/s_3^{gros}) \qquad (10),$$

the calculation of fracture porosity $\phi_f$ being given in stage 2.2.

According to an embodiment of the invention for which a characteristic matrix block dimension (a,b,c) has been calculated (see stage 2.2), an equivalent matrix permeability $keq_m^{ijk}$ in cell ijk conserving the value of the matrix-fracture exchange parameter is calculated as follows:

$$keq_m^{ijk} = G^2 k_m^{ijk} \qquad (11).$$

According to the invention, if the value of parameter P associated with the simplification (sub-)zone being considered indicates that all the families of the fracture network being considered are both substantially orthogonal to the layer being considered and substantially continuous towards the other layers of the formation, the values of the parameters defined above in principal direction 3 (that is $dir_3$) are not considered or are cancelled. Indeed, in this case, c being very large, this implies the non-existence of family 3 of simplified fractures, fractures whose normal is oriented in direction $dir_3$. In this case, only two vertical fracture families are generated, having directions of flow 1 and 2 as the normals in the case of a 2.5D type fracture network. In all the other cases, the equivalent parameters described above are calculated in the 3 directions. Three fracture families will be generated with directions of flow 1, 2 and 3 as the normals.

Figure 6:
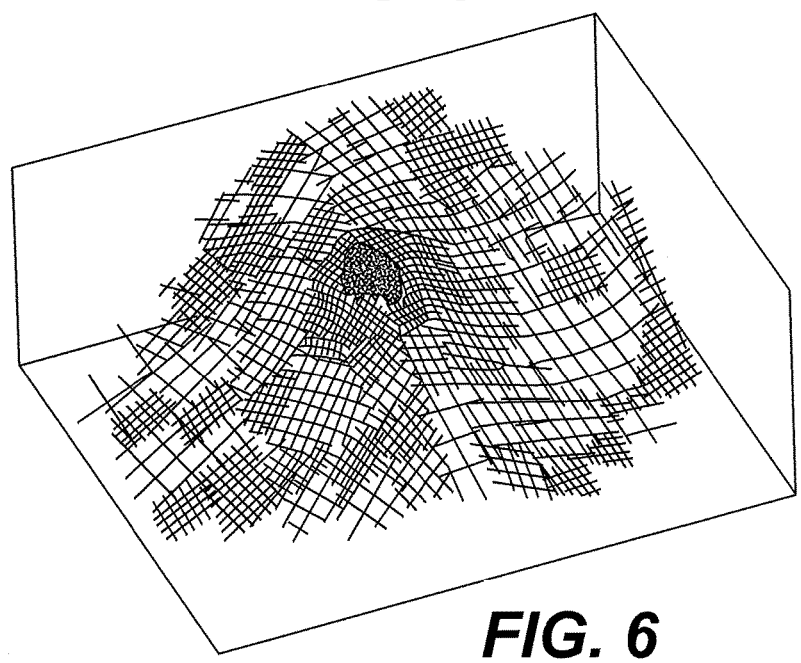
FIG. 6 shows the coverage between simplified fracture network models DFNs of neighboring simplification sub-zones.

Preferably, the fractures of the simplified networks obtained as described above are possibly extended outside the limits of the simplification (sub-)zones in order to guarantee sufficient partial "coverage" and therefore sufficient connectivity of the simplified networks of neighbouring sub-zones. Therefore, by following a test-proven procedure, the fractures of the simplified network DFNs can thus be extended by a length equal to 60% of the maximum spacing ($s_1^{gros}$, $s_2^{gros}$, $s_3^{gros}$) of the fractures of this network. Such a coverage between simplification (sub-)zones is for example illustrated in FIG. 6.

The fracture families making up the fracture network of a simplification zone or of a simplification sub-zone of a layer of the underground formation being studied are, at this stage, simplified by simplification zones or sub-zones respectively. More precisely, each simplification zone or sub-zone of a layer of the formation studied comprises a simplified fracture network DFNs characterized at least by a fracture spacing value, a fracture opening value and a permeability value. Furthermore, this simplified fracture network model is calculated by taking account of the orientation and the continuity of the fracture families of each simplification zone or sub-zone, through the determination of a parameter P. This simplified fracture network model DFNs can then be advantageously (in terms of computation time and in terms of accuracy as well) used for flow simulations, whether at reservoir scale or at the scale of a zone of influence of one or more wells.

Stages 1 and 2 defined above are repeated for each layer of the underground formation of interest prior to implementing stage 3.

3. Formation Fluid Exploitation

Once the above stages 1 and 2 have been repeated for each layer of interest of the formation being studied, an optimum exploitation scheme needs to be defined for the fluid of the formation studied, from the gridded representation for each layer, from the simplified fracture network model for each layer and from a flow simulator. An optimum exploitation scheme is understood to be an exploitation scheme allowing optimum exploitation of a fluid considered according to technical and economic predetermined criteria. It can be a scenario providing a high fluid recovery rate over a long exploitation time and requiring a limited number of wells. According to the invention, the fluid of the formation being studied is then exploited in accordance with this optimum exploitation scheme.

According to an embodiment of the invention, the reservoir engineer first constructs a flow model at reservoir scale, the flow model taking account of the simplified fracture network model. According to an embodiment of the invention using a flow simulation based on a "double medium" (also referred to as "double porosity") approach, two approaches can be implemented to construct the flow model:

1. Approach Based on the Conventional Double Porosity

Proposed by (Warren and Root, 1963), this approach assumes that any elementary volume (cell of the reservoir model) of the fractured reservoir is modelled in form of a set of identical parallelepipedic blocks, referred to as equivalent blocks, delimited by an orthogonal system of continuous uniform fractures oriented in the principal directions of flow. The fluid flow at the reservoir scale essentially occurs through the fractures, and fluid exchanges take place locally between the fractures and the matrix blocks. The methods described in the following documents, applied to the entire reservoir this time, can for example be used: FR-2,757,947 corresponding to U.S. Pat. No. 6,023,656, FR-2,757,957 corresponding to U.S. Pat. No. 6,064,944 and FR-2,918,179 corresponding to U.S. Pat. No. 8,078,405. These methods allow calculation of the equivalent fracture permeabilities and the equivalent block dimensions for each cell of the reservoir model. The result is then a grid filled with fracture and matrix equivalent properties and with equivalent block sizes. Solution of the flow is then achieved with a grid based on the gridded representation of the formation being studied, with a double medium simulator such as the PumaFlow software (IFP Energies ouvelles, France).

2. Approach Using a Simplified Network Over the Entire Reservoir

It is also possible to directly grid the simplified fracture network. This can be done by relying on patent applications FR-2,530,493 corresponding to U.S. Pat. No. 9,103,194 and FR-2,581,767 corresponding to US published application 2013/009,688,913. The grid can then be fed to a flow simulator based on a "double medium" type representation that can process unstructured grids, such as the PumaFlow software (IFP Energies ouvelles, France). Although costlier, this simulation is more precise, in particular in cases where the cells of the flow model are not oriented in the directions of flow.

The definition of an exploitation scheme for the fluid of the formation studied can select a type of recovery process (waterflood recovery for example), then in determining, for this type of process, the number, the geometry and the location (position and spacing) of the injection and production wells in order to best take account of the impact of the fractures on the progression of the fluids within the reservoir. In order to define an optimum exploitation scheme, different tests of various production scenarios can be carried out using a flow simulator. The exploitation scheme providing the best fluid recovery rate at the lowest cost is for example preferably selected.

According to a double medium type modelling, a so-called double medium flow simulator can be used to simulate the fluid production for a given exploitation scheme. At any time t of the simulation, the flow simulator solves all the flow equations specific to each cell of each one of the two grids of the model (equations involving the matrix-fracture exchange formula described above), and it thus delivers the values solution to the unknowns (saturations, pressures, concentrations, temperature, etc.) predicted at this time t. This solution provides knowledge of the amounts of oil produced and of the state of the reservoir (pressure distribution, saturations, etc.) at the time being considered. From a given exploitation scenario, the double medium representation of the reservoir and the formula relating at least one of the mass and energy exchange flux to the matrix-fracture potential difference, it is then possible to simulate the expected hydrocarbon production by means of the double medium flow simulator.

By selecting various scenarios, characterized for example by different respective injection and production well sites, and by simulating the fluid production for each one, the scenario allowing the production of the formation being considered to be optimized can be selected according to predetermined technical and economic criteria.

Then the fluid of the formation being considered is exploited according to the scenario allowing the reservoir production to be optimized, notably by drilling the injection and production wells defined by the optimum exploitation scheme, and allowing the fluid to be produced according to the recovery process defined by the optimum exploitation scheme.

Variants

Calculation of a Simplified Fracture Network Model on a Fine Grid

Figure 4:
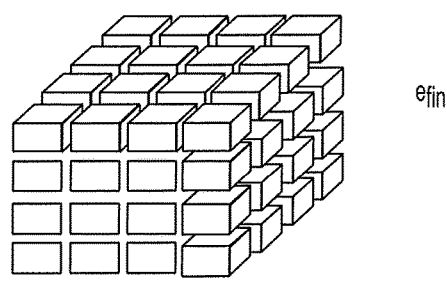
FIG. 4 illustrates a simplified fracture network DFNs on a fine grid.

According to an embodiment of the invention, in simplification stage 2.4, a first simplified fracture network model is calculated on a fine grid (sugar box type network) directly obtained from the equivalent permeability calculation. This network (FIG. 4) is characterized by fracture spacings corresponding to the matrix block dimensions identified in the zone or sub-zone, i.e. $s_1^{fin}=a$, $s_2^{fin}=b$, $s_3^{fin}=c$ in the 3 principal directions of permeability 1, 2, 3.

In this case, an additional parameter, the equivalent fracture opening parameter ($e^{fin}$) characterizing the fractures of this fine network (all the fractures of this fine network are assumed to have the same opening), is defined. Assuming the equality of porosities $\phi_f$ of the initial discrete fracture network model DFN and of the fine equivalent network, em is deduced from the fracture volume of the initial network DFN, $V_f^{init}$, and from the total rock volume $V_T$ as follows:

$$e^{fin} = \frac{1}{\left(\frac{1}{s_1^{fin}} + \frac{1}{s_2^{fin}} + \frac{1}{s_3^{fin}}\right)} \frac{V_f^{init}}{V_T} = \frac{1}{\left(\frac{1}{s_1^{fin}} + \frac{1}{s_2^{fin}} + \frac{1}{s_3^{fin}}\right)} \phi_f$$

As a matter of interest, the principal equivalent fracture permeabilities obtained from the aforementioned calculations are $k_1$, $k_2$ and $k_3$ in the principal directions 1, 2 and 3. The conductivities of the fractures of the fine equivalent network, $C_{f1}^{fin}$, $C_{f2}^{fin}$ and $C_{f3}^{fin}$ in these three directions of flow are deduced by writing the flux conservation per unit area of fractured medium:

$C_{f1}^{fin} = s_1^{fin} \cdot (-k_1+k_2+k_3)/2$ $C_{f2}^{fin} = s_2^{fin} \cdot (k_1-k_2+k_3)/2$ $C_{f3}^{fin} = s_3^{fin} \cdot (k_1+k_2-k_3)/2$ The numbers in indices f1, f2, f3 of the conductivity values indicate the direction of the normal of the simplified fracture. For example, $C_{f1}^{fin}$ is the conductivity to be assigned to the fractures of the fine network in direction dir$_c$, the principal direction of flow close to the X-axis of the reservoir grid.

Finally, the matrix medium between fractures has a permeability $k_m^{ijk}$.

Figure 5:
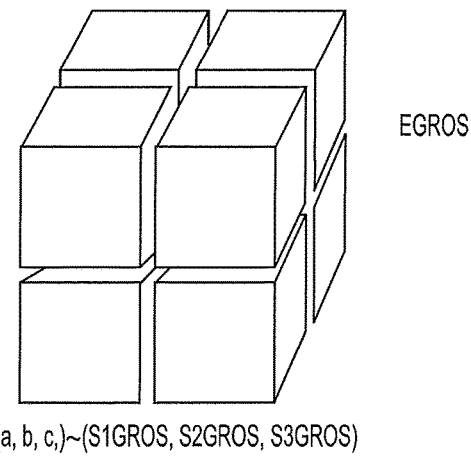
FIG. 5 illustrates a simplified fracture network model DFNs according to the invention.

This fine equivalent network (FIG. 4) is then replaced by the so-called "coarse" equivalent network (FIG. 5) comprising more spaced-out fractures to increase the degree of simplification with a view to later flow simulations. The geometric and flow properties of this coarse network are as follows:

fracture spacings $s_1^{gros}$, $s_2^{gros}$ and $s_3^{gros}$ such that:

$$s_1^{gros} = G \cdot s_1^{fin},$$

$$s_2^{gros} = G \cdot s_2^{fin},$$

$$s_3^{gros} = G \cdot s_3^{fin},$$

where G is a (fracture spacing) magnification coefficient of the network whose value can be determined as described in stage 2.4;

fracture conductivities $C_{f1}^{gros}$, $C_{f2}^{gros}$ and $C_{f3}^{gros}$ whose values allow conserving the fluxes per unit area of fractured medium, that is also the equivalent permeabilities, i.e.:

$$C_{f1}^{gros} = s_1^{gros} \cdot (-k_1 + k_2 + k_3)/2$$

$$C_{f2}^{gros} = s_2^{gros} \cdot (k_1 - k_2 + k_3)/2$$

$$C_{f3}^{gros} = s_3^{gros} \cdot (k_1 + k_2 - k_3)/2$$

or $$C_{f1}^{gros} = G \cdot C_{f1}^{fin}, \ C_{f2}^{gros} = G \cdot C_{f2}^{fin} \text{ and } C_{f3}^{gros} = G \cdot C_{f3}^{fin}$$

The numbers in indices f1, f2, f3 of the conductivity values indicate the direction of the normal of the simplified fracture. For example, $C_{f1}^{gros}$ is the conductivity to be assigned to the fractures of the coarse network in direction dir$_1$, the principal direction of flow close to the X-axis of the reservoir grid;

a fracture opening $e^{gros}$ allowing conserving again the fracture porosity $\phi_f$ of the initial network (equal to that of the coarse equivalent network):

$$\phi_f = e^{gros} \cdot (1/s_1^{gros} + 1/s_2^{gros} + 1/s_3^{gros}) = e^{fin} \cdot (1/s_1^{fin} + 1/s_2^{fin} + 1/s_3^{fin})$$

hence:

$$e^{gross} = e^{fin} \frac{\frac{1}{s_1^{fin}} + \frac{1}{s_2^{fin}} + \frac{1}{s_3^{fin}}}{\frac{1}{s_1^{gross}} + \frac{1}{s_2^{gross}} + \frac{1}{s_3^{gross}}} = G \cdot e^{fin}$$

a matrix permeability $keq_m^{ijk}$ conserving the value of the matrix-fracture exchange parameter, that is:

$$\lambda_{fin} = r_w^2 \frac{k_f^{ijk}}{k_f^{fin}} \left( \frac{\alpha}{S_1^{fin^2}} + \frac{\alpha}{S_2^{fin^2}} + \frac{\alpha}{S_3^{fin^2}} \right) =$$

$$\lambda_{grossier} = r_w^2 \frac{keq_m^{ijk}}{k_f^{gross}} \left( \frac{\alpha}{S_1^{gross^2}} + \frac{\alpha}{S_2^{gross^2}} + \frac{\alpha}{S_3^{gross^2}} \right)$$

where $\alpha$ is a constant and where the fracture equivalent permeabilities of the fine and coarse networks, equal, are here denoted by $k_f^{fin}$ and $k_f^{gros}$. A formula of the type as follows is then obtained:

$$keq_m^{ijk} = k_m^{ijk} \frac{\frac{1}{S_1^{fin^2}} + \frac{1}{S_2^{fin^2}} + \frac{1}{S_3^{fin^2}}}{\frac{1}{S_1^{gross^2}} + \frac{1}{S_2^{gross^2}} + \frac{1}{S_3^{gross^2}}} = G^2 k_m^{fin}$$

According to this variant embodiment of the invention, if the value of parameter P associated with the simplification (sub-)zone considered indicates that all the families of the fracture network considered are both substantially orthogonal to the layer considered and substantially continuous towards the other layers of the formation, the components along principal direction 3 (i.e. dir$_3$) of the parameters defined above are disregarded. Thus, only two vertical fracture families are generated, along directions of flow 1 and 2 in the case of a 2.5D type fracture network. In all the other cases, the equivalent parameters described above are calculated in the 3 directions and three fracture families will be generated, in directions of flow 1, 2 and 3.

Calibration of the Flow Properties of the Fractures

Prior to simulating the fluid production of the formation studied for different exploitation schemes, it can be advantageous to calibrate the flow properties of the fractures (fracture conductivity and opening), locally around the wells. Such a stage requires a well test simulation, from a well test simulator and a flow model. The flow model advantageously takes account of the simplified fracture network model determined in stage 2.

This type of calibration is well known to specialists. The method described in patent FR-2,787,219 corresponding to U.S. Pat. No. 6,842,725 can for example be used. The flow responses of some wells (transient or pseudo-permanent flow tests, interferences, flow rate measurement, etc.) are simulated on these models extracted from the reservoir model giving a discrete (realistic) representation of the fractures supplying these wells. The simulation result is then compared with the real measurements performed in the wells. If the results differ, the statistical parameters (PSF) describing the fracture networks are modified, then stages 1 and 2 described above are applied again prior to carrying out a new well test simulation. The operation is repeated until the well test simulation results and the measurements agree.

The results of these simulations allow calibration of (estimate) of the geometry and the flow properties of the fractures, such as the conductivities of the fracture networks of the reservoir being studied and the openings.

This optional stage allows determination of a more reliable simplified fracture network model as it enables construction of a flow model allowing existing measurements to be explained. Such a model can then be advantageously used to develop a flow model at the formation scale and to test various exploitation schemes through reservoir simulation.

Computer Program Product

Furthermore, the invention relates to a computer program product downloadable from at least one of a communication network recorded on a tangible computer-readable medium executable processor, comprising program code instructions for implementing the method according to the above description, when the program is executed on a computer.

Application Example

The features and advantages of the method according to the invention will be clear from reading the application example hereafter.

The present invention is applied to an underground formation having a single layer traversed by five wells with the layer containing a hydrocarbon type fluid and a fracture network wherein at least the orientation of one family leads to a parameter value P equal to 0 (3D type fracture network).

The goal of this application is to determine the optimum exploitation scheme, that is an exploitation scheme allowing optimum hydrocarbon recovery while meeting technical economic constraints. Among the exploitation schemes evaluated by flow simulation, a conventional exploitation scheme of five-spot injection type, with an injection well in the center of the formation to be exploited and four wells on the periphery, has been tested. Three simplification zones ZS1, ZS2, ZS3 of circular geometry have been defined around each well and for each layer of the formation.

Simplification zones ZS2 have then been divided into columnar type simplification sub-zones, and simplification zones ZS3 have been divided into locally homogeneous type simplification sub-zones.

Figure 7:
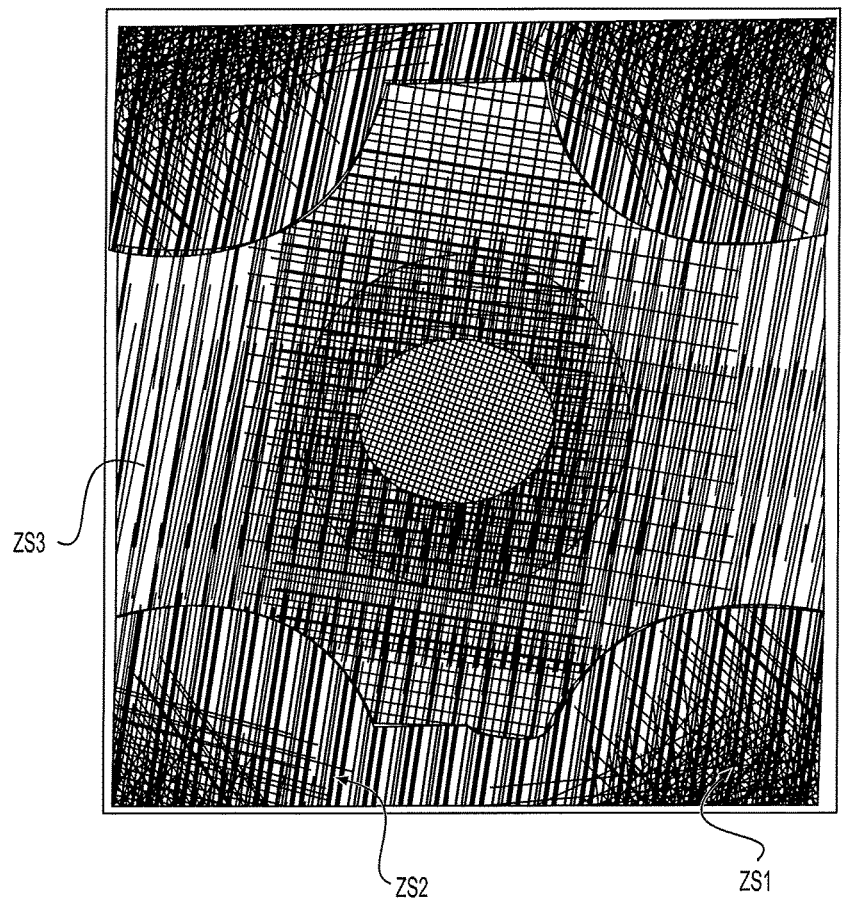
FIG. 7 illustrates a simplified fracture network model DFNs resulting from the implementation of the present invention in the case of a layer of an underground formation traversed by five wells.

FIG. 7 shows, for a layer of the formation, the limits of the simplification sub-zones of the simplified fracture network model resulting from the implementation of the invention according to the characteristics defined above. This figure notably shows zones ZS1 for which the grid is the finest (no simplification in zone ZS1), zones ZS2 for which the grid is of average size (division into columnar type simplification sub-zones) and zones ZS3 for which the grid is coarser (division into locally homogeneous type simplification sub-zones). Each one of these simplification sub-zones comprises a fracture opening, a fracture spacing, a permeability tensor and a conductivity tensor as determined according to the invention.

A flow simulation conducted on a non-simplified fracture network DNF (characterized by 350,000 fractures and having 2,560,000 intersections) turned out to be unworkable in practice as only 1% of the production time had been simulated after two weeks on a Dell Precision 5810 work station. With a simplified fracture network model DFNs obtained according to the method of the invention, the same simulation was completed in 12 hours on the same work station.

Thus, the simplification of a flow model according to the invention, in the case of any fractured medium, provides a significant gain in terms of computation time while preserving in the best possible way the flow properties around wells. This computation time gain can potentially allow testing more exploitation scenarios (exploitation schemes) for the fluid contained in the fractured medium, and thus determining an optimum exploitation scheme for the formation fluid, meeting technical and economic criteria as closely as possible.

The invention claimed is:

1. A method for exploiting a fluid within an underground formation comprising at least one layer traversed by a fracture network and by at least one well, wherein a gridded representation of the at least one layer is constructed from property measurements relative to the at least one layer in a zone of interest comprising a set of cells of the gridded representation relative to the layer which include the at least one well defined for the at least one layer comprising on each of the at least one layer performing steps of:

A. from the property measurements, characterizing the fracture network with statistical parameters, constructing from the parameters a discrete fracture network model;

B. defining at least a first simplification zone containing the at least one well, a second simplification zone having an inner boundary which is an outer boundary of the first zone and a third simplification zone having an inner boundary which is the outer boundary of the second simplification zone with all of the simplification zones of each of the wells covering all cells of the zone of interest;

C. from at least the statistical parameters, determining, for at each one of the simplification zones of the zone of interest, an equivalent permeability tensor and a value of a parameter characterizing an orientation and a continuity towards other layers of fractures of the network;

D. determining a simplification of the discrete fracture network model in each of the simplification zones as a function of the zone, of the equivalent permeability tensor and of the value of the parameter; and wherein from the gridded representation, the simplified fracture network model and a flow simulator, defining an optimum exploitation scheme for the fluid of the formation, and exploiting the fluid of the formation using the optimum exploitation scheme wherein the simplification zones are cylinders of a vertical axis and an elliptical section which are centered around the well and a major axis of one of the simplification zones is oriented in a chosen direction of flow, the chosen direction being determined from a diagonalization of the equivalent permeability tensor and wherein the optimum exploitation scheme is defined by determining a recovery method for the fluid, a number, a site and a geometry for injection and production wells which meet predetermined technical and economic criteria, and at least drilling the injection and production wells and producing the fluid according to the recovery method.

2. A method as claimed in claim 1, wherein a distance between two of the zones is determined according to a geometric progression of a constant ratio.

3. A method as claimed in claim 2, wherein simplification of the fracture network model is not carried out in the first simplification zone, a first simplification is carried out in the second zone and the second simplification is carried out in the third zone with the second simplification being greater than the first simplification.

4. A method as claimed in claim 3, wherein at least one of the second and the third simplification zones are divided into annular simplification sub-zones.

5. A method as claimed in claim 2, wherein at least one of the second and the third simplification zones are divided into annular simplification sub-zones.

6. A method as claimed in claim 2, wherein the second simplification zone is divided into columnar simplification sub-zones.

7. A method as claimed in claim 2, wherein the third simplification zone is divided into homogeneous simplification sub-zones.

8. A method as claimed in claim 7, wherein the simplification of the model is performed in two spatial directions if the parameter PC characterizes fractures orthogonal to the layers traversed by the fracture network and is continuous towards other layers.

9. A method as claimed in claim 1, wherein simplification of the fracture network model is not carried out in the first simplification zone, a first simplification is carried out in the second zone and the second simplification is carried out in the third zone with the second simplification being greater than the first simplification.

10. A method as claimed in claim 9, wherein at least one of the second and the third simplification zones are divided into annular simplification sub-zones.

11. A method as claimed in claim 9, wherein the second simplification zone is divided into columnar simplification sub-zones.

12. A method as claimed in claim 9, wherein the third simplification zone is divided into homogeneous simplification sub-zones.

13. A method as claimed in claim 1, wherein at least one of the second and the third simplification zones are divided into annular simplification sub-zones.

14. A method as claimed in claim 13, wherein the second simplification zone is divided into columnar simplification sub-zones.

15. A method as claimed in claim 13, wherein the third simplification zone is divided into homogeneous simplification sub-zones.

16. A method as claimed in claim 1, wherein the second simplification zone is divided into columnar simplification sub-zones.

17. A method as claimed in claim 16, wherein the third simplification zone is divided into homogeneous simplification sub-zones.

18. A method as claimed in claim 1, wherein the third simplification zone is divided into homogeneous simplification sub-zones.

19. A method as claimed in claim 1, wherein a parameter P is determined for at least each one of the simplification zone, by using:
   a value of a parameter PO measuring a spatial orientation of the fractures of the layer according to a formula:
   at least one of $$PO = \frac{dev^2}{90^2} - 2\frac{dev}{90} + 1 \text{ with } dev = \arccos(\vec{dir}_3 \cdot \vec{z}) * \frac{180}{(PI)'}$$

and/or
   a value of a parameter PC measuring continuity of the fractures of the layer towards other layers according to a formula:

$$PC = \frac{k_3}{(k_1 + k_2)'}$$

with $k_1$, $k_2$ and $k_3$ being eigenvalues of the permeability tensor after diagonalization;
   PI is a $\pi$ radians, $dir_3$ is a principal direction of flow after diagonalization and z is a vertical axis.

20. A method as claimed in claim 19, wherein the simplification of the model is performed in three spatial directions if the parameter P characterizes fractures orthogonal to at least one of the layers and is continuous towards other layers.

21. A method as claimed in claim 1, wherein the simplification includes calculating at least a fracture spacing value for the fractures, an opening value for the fractures and a permeability value.

22. A non-transitory computer-readable medium storing computer executable instructions which when executed by a processor, perform the method as claimed in claim 1.

* * * * *